(12) United States Patent
Zhao et al.

(10) Patent No.: US 10,285,613 B2
(45) Date of Patent: May 14, 2019

(54) APPARATUS AND METHOD FOR DETERMINING THE OCCURRENCE OF A QRS COMPLEX IN ECG DATA

(71) Applicant: KONINKLIJKE PHILIPS N.V., Eindhoven (NL)

(72) Inventors: Dan Zhao, Shanghai (CN); Wei Li, Shanghai (CN)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 16/043,237

(22) Filed: Jul. 24, 2018

(65) Prior Publication Data
US 2018/0325404 A1    Nov. 15, 2018

Related U.S. Application Data

(62) Division of application No. 14/762,492, filed as application No. PCT/EP2014/078625 on Dec. 19, 2014, now Pat. No. 10,058,260.

(30) Foreign Application Priority Data

Dec. 20, 2013    (WO) ................ PCT/CN2013/090108
Feb. 5, 2014     (EP) ..................................... 14153955

(51) Int. Cl.
   *A61B 5/0452*    (2006.01)
   *A61B 5/00*      (2006.01)
   (Continued)

(52) U.S. Cl.
   CPC ............ *A61B 5/0452* (2013.01); *A61B 5/044* (2013.01); *A61B 5/0408* (2013.01);
   (Continued)

(58) Field of Classification Search
   CPC ... A61B 5/0452; A61B 5/7221; A61B 5/0472; A61B 5/746; A61B 5/0408; A61B 5/044; A61B 5/04017; A61B 5/7203
   See application file for complete search history.

(56) References Cited

U.S. PATENT DOCUMENTS

| 4,987,901 A | 1/1991 | Kunig |
| 5,817,027 A | 10/1998 | Arand et al. |

(Continued)

FOREIGN PATENT DOCUMENTS

| CN | 1163741 A | 11/1997 |
| CN | 103110417 A | 5/2013 |

(Continued)

OTHER PUBLICATIONS

Forlini et al: "ST-Segment Isolation and Quantification As a Means of Improving Diagnostic Accuracy in Treadmill Stress Testing"; American Heart Journal, Oct. 1975, vol. 90, No. 4, PO\P. 431-438.

(Continued)

*Primary Examiner* — Christopher Koharski
*Assistant Examiner* — Roland Dinga (57) ABSTRACT

The present invention provides apparatus and a method for determining the occurrence of a QRS complex in ECG data. According to an aspect of the present invention, an apparatus is proposed for determining the occurrence of a QRS complex in ECG data by utilizing a first, second and third set of ECG data that are acquired by respectively electrode leads II, V4 and V5 and by determining whether a QRS complex has been detected within the predefined temporal window in at least two of the first, second and third sets of ECG data. According to another aspect of the present invention, an apparatus is proposed for determining the occurrence of a QRS complex in ECG data by utilizing three sets of ECG data whose signal quality values V are the smallest three of the first to twelfth sets of ECG data that are acquired by (Continued)

respectively the standard 12 electrode leads and by determining whether a QRS complex has been detected within the predefined temporal window in at least two of the three sets of ECG data. The two apparatus of the present invention may improve the accuracy of QRS detection, which has been proved by clinical testing.

4 Claims, 6 Drawing Sheets

(51) Int. Cl.
*A61B 5/0472* (2006.01)
*A61B 5/04* (2006.01)
*A61B 5/0408* (2006.01)
*A61B 5/044* (2006.01)

(52) U.S. Cl.
CPC ........ *A61B 5/04017* (2013.01); *A61B 5/0472* (2013.01); *A61B 5/7221* (2013.01); *A61B 5/746* (2013.01); *A61B 5/7203* (2013.01)

(56) References Cited

U.S. PATENT DOCUMENTS

| | | | |
|---|---|---|---|
| 5,827,196 A | 10/1998 | Yeo et al. |
| 6,263,235 B1 | 7/2001 | Kaiser et al. |
| 6,358,214 B1 | 3/2002 | Tereschouk |
| 6,564,090 B2 | 5/2003 | Taha et al. |
| 6,668,195 B2 | 12/2003 | Warman |
| 7,974,684 B2 | 7/2011 | Stewart |
| 2005/0107836 A1 | 5/2005 | Noren |
| 2008/0183093 A1 | 7/2008 | Duann |
| 2011/0319777 A1 | 12/2011 | Mehrotra |
| 2013/0060156 A1 | 3/2013 | Gregg |

FOREIGN PATENT DOCUMENTS

| | | |
|---|---|---|
| JP | H09173310 A | 7/1997 |
| JP | 1170089 | 3/1999 |
| JP | 2003159226 A | 6/2003 |
| JP | 2007535392 A | 12/2007 |
| JP | 2014171677 A | 9/2014 |
| RU | 94037134 A | 7/1996 |
| RU | 2009116480 A | 11/2010 |
| WO | 2005104937 A2 | 11/2005 |
| WO | 2013054242 A1 | 4/2013 |

OTHER PUBLICATIONS

Philips:"Improving ECG Quality"; Application Note, Published 2008,. 6 Page Document.

Sassi et al: "T-Wave Alternans: Lessons Learned From a Biophysical ECG Model": Journal of Electrocardiology 45 (2012), pp. 566-570.

Kligfield: "The Centennial of the Einthoven Electrocardiogram"; Journal of Electrocardiology, vol. 35, Supplement 2002, pp. 123-129.

Alfonso: "ECG QRS Detection"; Chapter 12, pp. 236-265, "Biomedical Digital Signal Processing: C-Language Examples and Laboratory Experiments for the IBM PC"; Willis J. Tompkins, Editor, University of Wisconsin-Madison, 2000.

Kligfield et al: "Recommendations for the Standardization and Interpretation of the Electrocardiogram"; Journal of the American Heart Association, Inc, vol. 49, No. 10, 2007, pp. 1109-1127.

Zeelenberg et al: "Evaluation and Optimisation of an Existing Arrythmia Detection System by Using an Annotated ECG Database"; Computers in Cardiology, 1981, pp. 103-108.

APPARATUS AND METHOD FOR DETERMINING THE OCCURRENCE OF A QRS COMPLEX IN ECG DATA

This application is a divisional of co-pending U.S. patent application Ser. No. 14/762,492 filed on Jul. 22, 2015 and entitled "APPARATUS AND METHOD FOR DETERMINING THE OCCURRENCE OF A QRS COMPLEX IN ECG DATA", which is the U.S. National Phase application under 35 U.S.C. § 371 of International Application No. PCT/EP2014/078625, filed on Dec. 19, 2014, which claims the benefit of European Patent Application No. 14153955.1, filed on Feb. 5, 2014, and Chinese Patent Application No. PCT/CN2013/090108, filed on Dec. 20, 2013. These applications are hereby incorporated by reference herein.

FIELD OF THE INVENTION

The present invention relates to ECG monitoring, more particularly to apparatus and a method for determining the occurrence of a QRS complex in ECG data acquired from a subject being monitored, and to an ECG monitoring system utilizing the same.

BACKGROUND OF THE INVENTION

Nowadays, the electrocardiogram (ECG) is one of the most commonly used tools in clinical practice, since it is a way to measure and diagnose abnormal rhythms of the heart and it is a fundamental part of many clinical instruments such as the cardiotachometer and the arrhythmia monitor.

A typical ECG waveform consists of a P wave indicating atrial depolarization, a QRS complex indicating ventricular depolarization, a T wave indicating ventricular repolarization, and a possible U wave in some cases indicating the extension of the repolarization. The dominant activity of an ECG usually relates to the QRS complex in real time, using medical instruments such as an arrhythmia monitoring system, an ECG stress test system, cardiographs. Accurate detection of the QRS complex of an ECG is significant for all these clinical applications, for example, in an arrhythmia monitoring system, significant false negative and false positive rates can result from faulty QRS detection.

Over the past few years, many techniques have been developed to detect the QRS complex, including power spectrum analysis, bandpass filtering, differentiation, template matching, and waveform feature-dependent real-time techniques. The diversity and complexity of the samples determine the difficulty of accurate QRS detection. However, the conventional real-time detection algorithms are still not very satisfactory in terms of accuracy of detection.

Conventionally, in practical applications, the apparatus used for QRS detection usually selects the electrode lead which contains apparent complex features, for example, one of the standard limb leads, lead II of the standard twelve electrodes recommended by the American Heart Association (AHA). And in some cases, global detection techniques may be used, for example, perpendicular leads II, aVF and V5 are used together to guarantee detection reliability.

However, in a stress testing system, the rapidly increasing muscle activity and mechanical forces acting on the electrode leads usually lead to excessive muscle noise which brings about an unrecognizable waveform. These adverse random artifacts degrade the accuracy of QRS detection.

Figure 1:
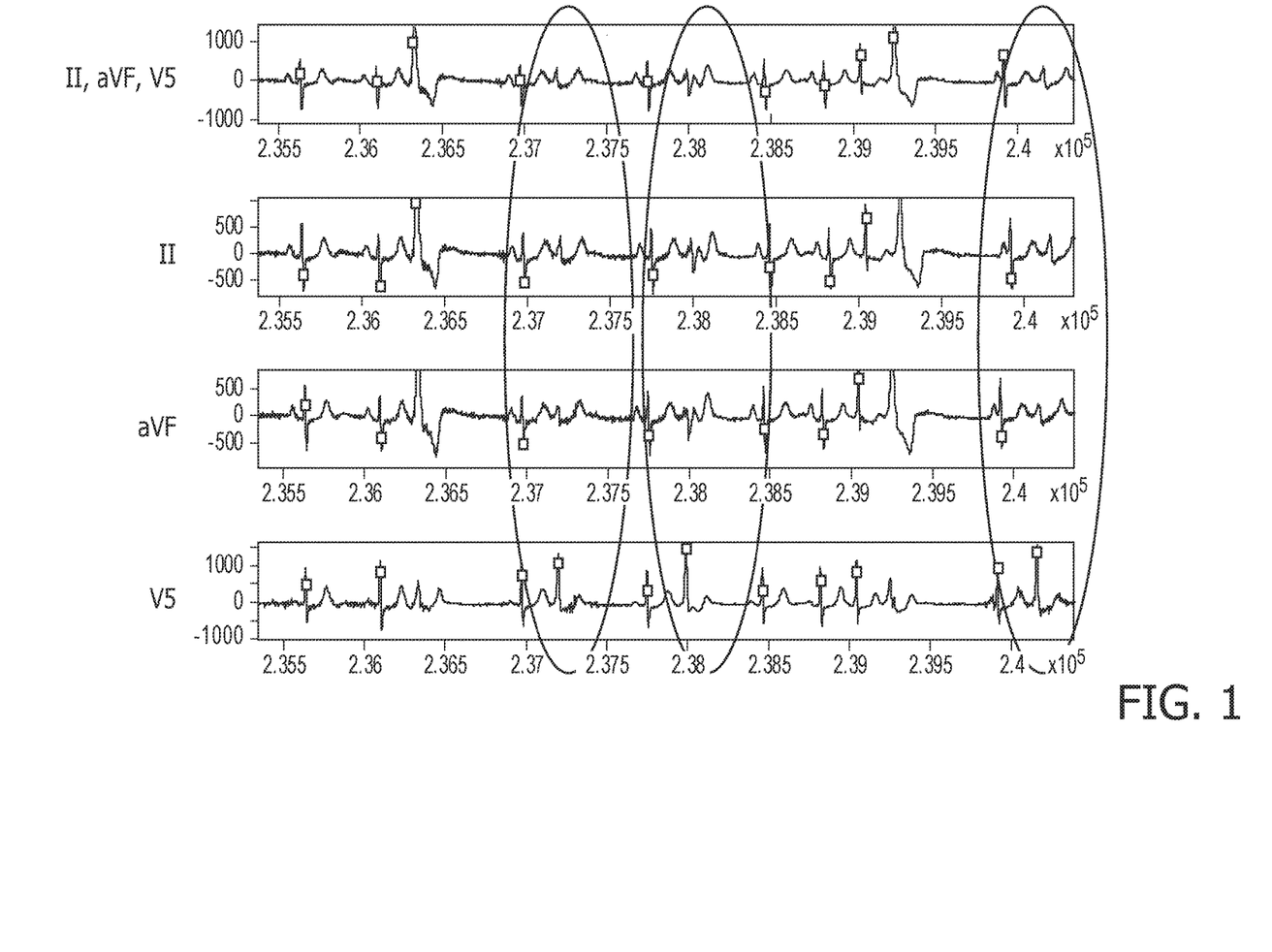
FIG. 1 shows a patient case in a stress testing system conducted at Hoag Hospital, Newport Beach, Calif.

The deficiencies of the conventional techniques for QRS detection may be clearly understood from FIG. 1, which shows a patient case in a stress testing system conducted at Hoag Hospital, Newport Beach, Calif. The high frequency, low frequency and AC noise of the ECG data has been filtered out by some pre-processing filtering technique. From the top to the bottom, the four waveforms in FIG. 1 are beat detection by using global detection techniques, based on the selected leads II, aVF and V5; detection using lead II only; detection using lead aVF only; and detection using lead V5 only, respectively.

It can be clearly seen that even using global detection techniques, QRS detection is not accurate enough and some important waveform features may be missed, for example, the PVC-like widened QRS complex in leads II, aVF.

SUMMARY OF THE INVENTION

Therefore, due to the deficiencies of the conventional techniques for QRS detection, there is a need to provide an improved method and apparatus for determining the occurrence of a QRS complex in ECG data with improved detection accuracy, especially in a stress testing system.

To this end, the inventors of the present invention have conducted a large number of clinical researches and experiments, and found two novel ways for QRS complex detection, which improve the real-time detection accuracy of the QRS complex in ECG data of the subject.

Specifically, instead of using one lead, for example lead II, or instead of using leads II, aVF and V5 as global detection in the conventional apparatus, the one type of apparatus proposed for QRS detection uses the ECG data acquired by electrode leads II, V4 and V5, since the inventors have found that these three leads are not only more suitable for accurate observation of ventricular activity but also are complementary to each other in terms of peak value detection; therefore the combination of the three leads would improve the detection sensitivity for the abnormal QRS complex, particularly for the patient cases of PVC, LBBB, RBBB or others.

Therefore, in accordance with an aspect of the present invention, an apparatus is proposed for determining the occurrence of a QRS complex in ECG data acquired from a subject being monitored, said apparatus comprising a receiving unit configured to receive a first, second and third set of ECG data that are acquired by respectively electrode leads II, V4 and V5 attached to the subject; a detecting unit configured to evaluate the first, second and third set of ECG data so as to detect whether or not a QRS complex occurs within a predefined temporal window in the respective set of ECG data; and an output configured to output a message indicating an occurrence of a QRS complex within the predefined temporal window if a QRS complex has been detected within the predefined temporal window in at least two of the first, second and third set of ECG data.

In this way, the occurrence of a QRS complex may be determined more accurately, and the increased accuracy with which the QRS complex is detected enables the ECG data to be improved compared to the conventional way of utilizing the ECG data acquired by lead II alone or by leads II, aVF and V5 as global detection. Thus, the final ECG report output by the ECG monitoring system for clinical diagnosis, which is in accordance with the QRS detection result from the apparatus of the present invention, will be more accurate.

Furthermore, in the present embodiment, not only the three leads II, V4 and V5 used for QRS detection are different from those used in the conventional global detection technique, but also the determination of the occurrence of the QRS complex in the present embodiment is based on a majority criterion, thereby enabling to avoid the false determination of the occurrence of a QRS complex if only one of the three leads detects the QRS complex due to an abnormal situation, and enabling to avoid wrong determination of the occurrence of a true QRS complex. Therefore, it may further improve the accuracy for QRS detection.

Furthermore, as another type of apparatus for QRS detection, the inventors of the present invention found that utilizing signal quality estimation techniques to select the most appropriate leads as the promising leads may enhance the detection accuracy in a smart way.

Therefore, in accordance with another aspect of the present invention, there is proposed an apparatus for detecting the occurrence of a QRS complex in ECG data acquired from a subject being monitored, comprising:

a receiving unit configured to receive a first to twelfth sets of ECG data that are acquired by respectively the standard twelve electrode leads attached to the subject;

a detecting unit configured to evaluate the first to twelfth sets of ECG data so as to detect whether or not a QRS complex occurs within a predefined temporal window in the respective set of ECG data;

a calculation unit configured to derive a first to twelfth signal quality values V respectively for each of the first to twelfth sets of ECG data by calculating the ratio of standard deviation of N consecutive waveforms in the respective set of ECG data to a reference standard deviation of the respective set of ECG data or by calculating the ratio of the signal energy ratio (SNR) of N consecutive waveforms in the respective set of ECG data to a reference SNR of the respective set of ECG data, wherein the reference standard deviation and the reference SNR of the respective set of ECG data are predetermined from respectively a first to twelfth sets of ECG data that are acquired by respectively the standard twelve electrode leads at the pre-exercise stage;

a comparison unit configured to compare the first to twelfth signal quality values V and determine three sets of ECG data whose signal quality values V are the smallest among the first to twelfth sets of ECG data; and an output configured to output a message indicating an occurrence of a QRS complex within the predefined temporal window if a QRS complex has been detected within the predefined temporal window in at least two of the determined three sets of ECG data.

As can be seen from the above, the second type of apparatus is different from the first type in that the three electrode leads are not fixedly selected but are selected according to the signal quality of the ECG data acquired by the leads. From a theoretical point of view, the performance of the second type of apparatus is better than that of the first type due to the adaptive feature. However, from a complexity point of view in practical application, the first type of identifier is more suitable, considering the compromise between detection accuracy and complexity requirements.

Similarly, in the present embodiment, not only are the three leads used for QRS detection selected according to the signal quality and are different from those used in the conventional global detection technique, but also the determination of the occurrence of a QRS complex in the present embodiment is based on a majority criterion, enabling to avoid misdetermination of the occurrence of a QRS complex if only one of the three leads detects the QRS complex due to an abnormal situation, and enabling to avoid misdetermination of the occurrence of a true QRS complex. Therefore, it may further improve the QRS detection accuracy.

The performance of the invented two apparatus has been verified by clinical testing on volunteer cases and patient cases at Hoag Hospital, Newport Beach, Calif. The total error rate of 0.19 percent is analyzed by using about 28.960 beats, and the sensitivity of the invented apparatus for QRS detection is 99.81 percent.

Furthermore, in both proposed apparatus, besides the smart selection purpose utilized in the second solution, the signal quality estimation technique may also be used to trigger a warning message which is a good indicator for the clinicians that unacceptable signal quality of the collected ECG data requires attention or action.

In this way, the clinical staff may be notified in time that unsatisfactory ECG data has been collected and they may then timely check whether this is due to the loss of contact between the leads and the subject or due to other reasons.

In accordance with still another aspect of the present invention, there is further proposed an ECG monitoring system, which comprises: an ECG signal acquisition unit configured to acquire and preprocess raw ECG data from the standard twelve electrode leads attached to a subject; an ECG signal processing unit configured to process the preprocessed data from the ECG signal acquisition unit to derive an ECG report comprising QRS complex information and other ECG feature information, wherein the ECG signal processing unit comprises any one type of the above mentioned two apparatus for detecting the occurrence of a QRS complex in ECG data acquired from a subject being monitored; an output unit configured to output the ECG report by displaying or printing the ECG report; and a storage unit configured to store the preprocessed data from the ECG signal acquisition unit and the ECG report.

As mentioned above, since the occurrence of a QRS complex may be determined more accurately, and accordingly the improved accuracy of detection of the QRS complex enables the ECG data to be improved compared with the conventional way of utilizing the ECG data acquired by lead II alone or by leads II, aVF and V5 as global detection, the final ECG report output by the ECG monitoring system for clinical diagnosis, which is produced in accordance with the result of a QRS detection from the apparatus of the present invention, would be more accurate compared with the ECG report output by the ECG monitoring system utilizing the conventional apparatus for QRS detection.

Various aspects and features of the disclosure are described in further detail hereinbelow. These and other aspects of the invention will be apparent from and elucidated with reference to the embodiment(s) described hereinafter.

DESCRIPTION OF THE DRAWINGS

The present invention will be described and explained in more detail hereinafter in combination with embodiments and with reference to the drawings, wherein.

The same reference signs in the figures indicate similar or corresponding features and/or functionalities.

DETAILED DESCRIPTION OF THE EMBODIMENTS

The present invention will be described with respect to particular embodiments and with reference to certain drawings, but the invention is not limited thereto but is limited only by the claims. The drawings described are only schematic and are non-limiting. In the drawings, the size of some of the elements may be exaggerated and not drawn to scale for illustrative purposes.

Figure 2:
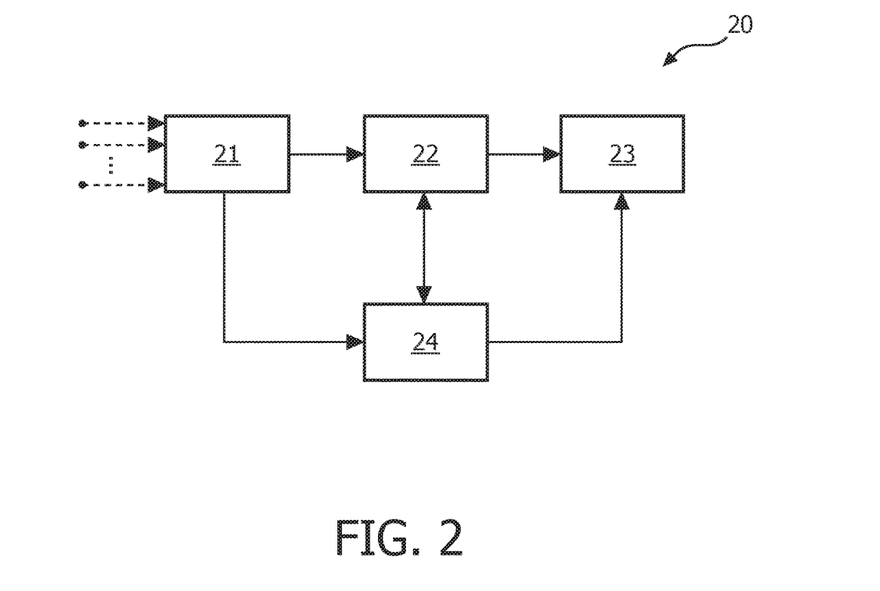
FIG. 2 is a block diagram of an ECG monitoring system.

FIG. 2 illustrates the block diagram of an ECG monitoring system 20, which includes an ECG signal acquisition unit 21, an ECG signal processing unit 22 and an output unit 23.

As shown in FIG. 2, a plurality of electrode leads, for example 12 leads, recommended by the American Heart Association (AHA), are simultaneously applied and attached to the subject, for example the patient, to collect the electrical activity of the heart through the surface of the skin. The ECG signal acquisition unit 21 usually performs the pre-processing, such as amplification and digitization, of the collected electrical signals from the body by using the electrode leads.

The system 20 may further comprise a storage unit 24, and the pre-processed ECG data from the ECG signal acquisition unit 21 may be digitally stored in the storage unit 24 and also output to the ECG signal processing unit 22, where the pre-processed ECG signal may be processed by appropriate filtering, dominant activity identification, feature analysis and measurements, to generate a QRS complex and other ECG feature information, which will finally be displayed or printed in an ECG rhythm/Auto report by the output unit 23.

Figure 3:
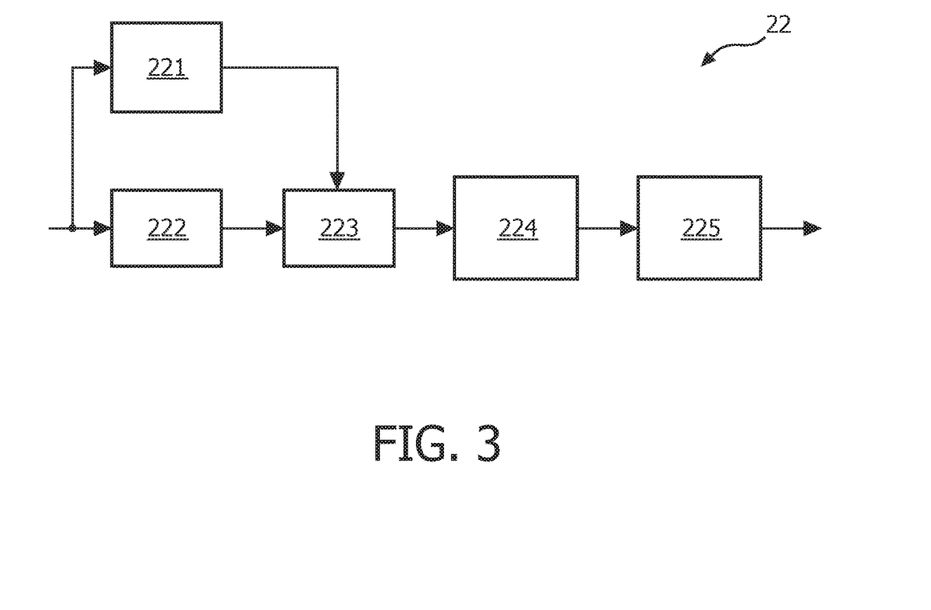
FIG. 3 shows the detailed structure of an ECG signal processing unit contained in the ECG monitoring system of FIG. 2.

FIG. 3 illustrates the detailed structure of the ECG signal processing unit 22 comprised in the ECG monitoring system 20 of FIG. 2.

As shown in FIG. 3, in addition to an apparatus 224 for determining the occurrence of a QRS complex in ECG data acquired from a subject being monitored and a deriving unit 225 for deriving other ECG feature information, the ECG signal processing unit 22 may further comprise several units to reduce the noise of the pre-processed ECG data before the data is input into the apparatus 224 and the deriving unit 225.

The reason, as can be understood by the person skilled in the art, is that biological signals may include substantial amounts of noise, which usually result in degraded and even unacceptable signal quality for beat analysis, classification and clinical diagnosis, particularly during the ergometric test such as the treadmill exercise and the bicycle ergometer test. Artifacts in an ECG have different kinds of characteristics, for example, low-frequency noise and high-frequency noise. From another point of view, artifacts can be classified into artifacts with fixed frequency characteristics and artifacts with random characteristics.

Accordingly, to reduce these noises, the ECG signal processing unit 22 may further comprise a power-line frequency analysis unit 221, a band-pass filtering unit 222 configured to filter the low frequency and high frequency noise in the ECG data, and an AC filtering unit 223 configured to filter the effect of the power-line interference in accordance with the identification result of the power line frequency analysis unit 221.

As is well-known in the art, although the power-line interference is usually classified as artifact with fixed frequency at 50/60 Hz, environmental conditions may disrupt the steady state or even cause harmonic components. Therefore, the power-line frequency analysis unit 221 is utilized to identify the base frequency component and the existence of the corresponding harmonic components for the AC filtering unit 223 to attenuate the adverse effect of the power-line interference. The band-pass filtering unit 222 provides a conventional tool to reduce the low frequency and high frequency noise. According to the different application requirements, the recommended bandwidth that contains significant ECG signal information may be considered, for example, to range from 0.05 Hz to 150 Hz for adolescents, and a bandwidth up to 250 Hz is needed for pediatric cases. After the ECG signal has passed through the band-pass filtering and AC filtering stages, its signal-to-noise ratio increases, which definitely improves the overall sensitivity of the apparatus 224 for QRS detection and the performance of the deriving unit 225 for deriving other ECG feature information.

In the following, two types of apparatus 224 according to the present invention, which improve the accuracy of QRS complex detection in the ECG, are proposed and elaborated in detail in conjunction with figures.

Figure 4:
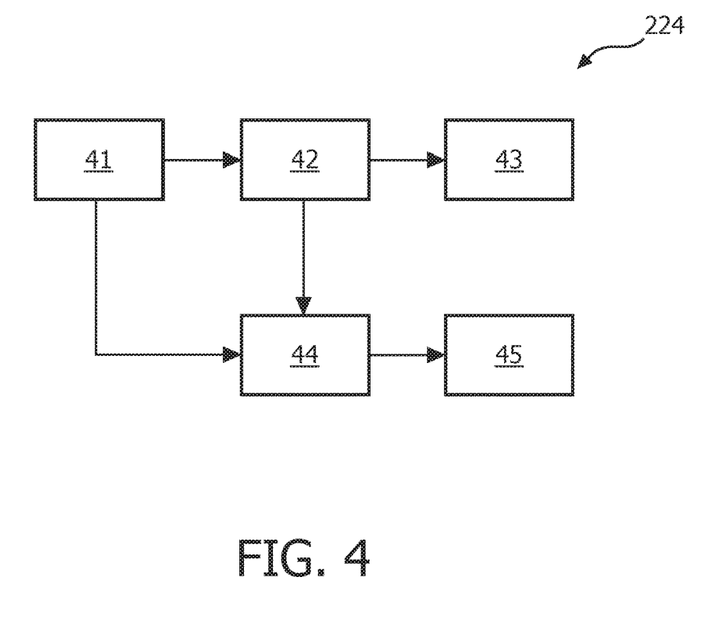
FIG. 4 is a block diagram of an apparatus for determining the occurrence of a QRS complex in ECG data according to an embodiment of the present invention.

FIG. 4 is a block diagram of an apparatus 224 for determining the occurrence of a QRS complex in ECG data according to an embodiment of the present invention. Hereinafter, details of the apparatus 224 will be described in conjunction with FIG. 5, which shows a flow chart of the method 50 performed by the apparatus 224 according to the present embodiment.

As can be seen from FIG. 4, the apparatus 224 of the present embodiment comprises a receiving unit 41, a detecting unit 42, and an output 43.

Figure 5:
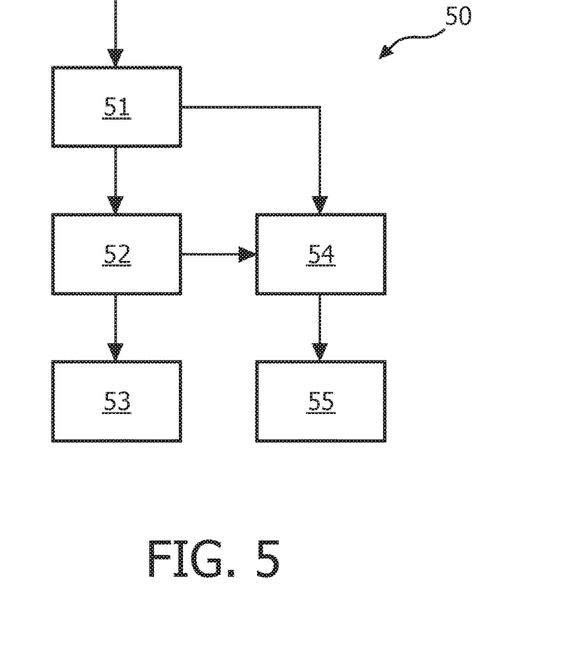
FIG. 5 shows a flow chart of the method for determining the occurrence of a QRS complex in ECG data according to the present embodiment.

First, of the 12 sets of ECG data acquired respectively by the standard twelve electrode leads attached to the subject, the receiving unit 41 of the apparatus 224 of the present embodiment receives three sets of ECG data that are acquired respectively by electrode leads II, V4 and V5 (step 51 in the flow chart of FIG. 5).

For example, the receiving unit 41 receives a first set of ECG data that is acquired by electrode lead II, a second set of ECG data acquired by electrode lead V4, and further a third set of ECG data acquired by electrode lead V5. As shown in FIG. 3, in an embodiment, the filtered ECG data from the AC filtering unit 223 may be used as the input of the apparatus 224, so that the accuracy of QRS complex detection may be improved compared to the case in which the raw ECG data is used.

Next, the detecting unit 42 evaluates the first, second and third sets of ECG data so as to detect whether or not a QRS complex occurs within a predefined temporal window in the respective set of ECG data (step 52 in FIG. 5). In an embodiment, the predefined temporal window may be selected as 80 ms, which may be adjusted according to the particular situation of the subject.

In detail, the detecting unit 42 may utilize the QRS detector to detect the filtered data from each of the three leads, after which the predefined temporal window may be applied to the detected QRS complex. If within the predefined temporal window there are at least two leads which have detected a QRS complex successfully, the output 43 of the apparatus may output a message indicating an occurrence of a QRS complex within the predefined temporal window (step 53 in FIG. 5).

In this way, the apparatus 224 may confirm the reliability of the detected QRS beats and may further determine the beat location accordingly.

In this embodiment, unlike the conventional way of QRS detection, the limb and chest leads II, V4 and V5 are selected as the promising leads for dynamic beat identification; these three leads are not only more suitable for accurate observation of ventricular activity but they also are complementary to each other in terms of peak value detection, therefore the combination of the three leads would improve the sensitivity for detection of an abnormal QRS complex, particularly for the patient cases of PVC, LBBB, RBBB or others.

Further, in the present invention, not only the three leads used for QRS detection are different from those used in the conventional global detection technique, but also the determination of the occurrence of a QRS complex is based on a majority criterion, thus enabling to avoid misdetermination of the occurrence of a QRS complex if only one of the three leads detects the QRS complex due to an abnormal situation. Therefore, it may further improve the accuracy of QRS detection.

As shown in FIG. 4, optionally, the apparatus 224 may further comprise a calculation unit 44 configured to derive a first, second and third signal quality value V respectively for each of the first, second and third set of ECG data.

The AC filtered data and the detected QRS complex location information are provided to the calculation unit 44 in parallel, which performs(?) a statistical signal quality evaluation.

Specifically, in one embodiment, the calculation unit 44 may first calculate the standard deviation of N consecutive waveforms in a respective set of ECG data. Similarly, the reference standard deviation of the respective set of ECG data may be predetermined from respectively a first, second and third set of ECG data that are acquired respectively by electrode leads II, V4 and V5 at the pre-exercise stage, for example the stage during which the subject is in a state of rest, so that the reference standard deviation may represent the normal state of the ECG data acquired by each lead and be used as a basis for determining the fluctuation of the ECG data acquired during real testing in the normal state.

With this standard deviation and reference standard deviation of respective sets of ECG data, the signal quality value for each set may be derived by calculating the ratio of the standard deviation of N consecutive waveforms in respective sets of ECG data to the reference standard deviation of respective sets of ECG data (step 54 in FIG. 5).

As will be easily understood by the person skilled in the art, although the standard deviation of the acquired ECG data may be used to calculate the signal quality value thereof, it is not limed thereto. For example, the variance of the acquired ECG data may also be used to derive the signal quality value.

Further, another example of signal quality estimation may be implemented by using ECG spectrum analysis, as a standard ECG signal for clinical application usually has a bandwidth in the range of 0.05 to 100 Hz, and the energy of a QRS complex is in the range of 5 to 40 Hz. Therefore, the signal energy ratio (SNR) may be calculated as follows:

$$SNR = \frac{Energy_{[5Hz, 40Hz]}}{Energy_{[0.05Hz, 100Hz]}}$$

And, similarly, a SNR reference value may be determined by means of the mean variance during the pre-exercise stage or learn mode. Finally, using the obtained SNR and reference SNR, an SNR ratio can be determined according to:

$$ratio = \frac{SNR}{reference\ SNR}$$

The apparatus 224 may further comprise an interface unit 45, which will output a warning message when one of the first, second and third signal quality values V is greater than a predetermined threshold (step 55 in FIG. 5).

In this way, the clinical staff may be notified in time that unsatisfactory ECG data has been collected and they may then timely check whether this is due to the loss of contact between the leads and the subject or due to other reasons.

Figure 6:
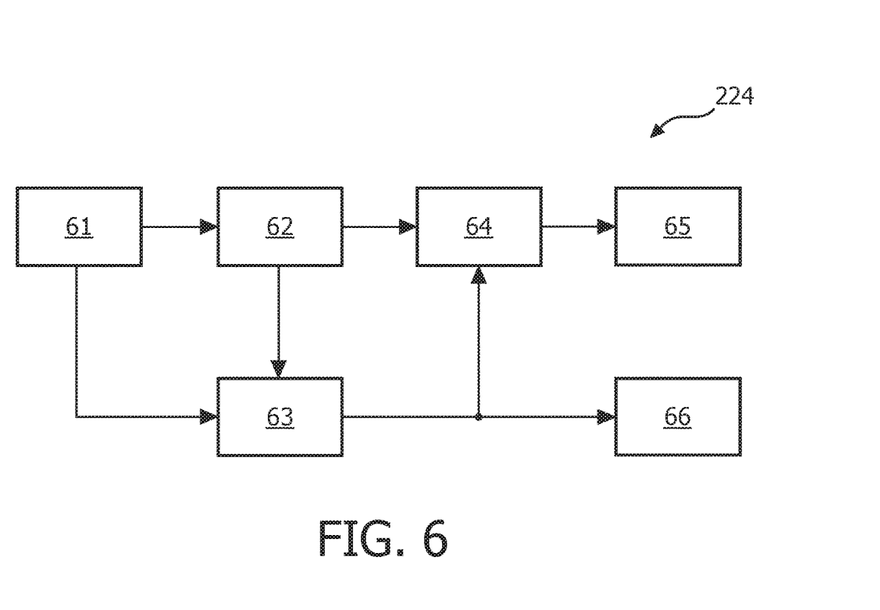
FIG. 6 is a block diagram of an apparatus for determining the occurrence of a QRS complex in ECG data according to another embodiment of the present invention.

FIG. 6 is a block diagram of an apparatus 224 for determining the occurrence of a QRS complex in ECG data according to another embodiment of the present invention.

In the following, details of the apparatus 224 will be described in conjunction with FIG. 7, which shows a flow chart of the method 70 for determining the occurrence of a QRS complex in ECG data according to the present embodiment.

As can be seen from FIG. 6, the apparatus 224 for determining the occurrence of a QRS complex in ECG data in accordance with the present embodiment comprises a receiving unit 61, a detecting unit 62, a calculation unit 63, a comparison unit 64 and an output 65.

Figure 7:
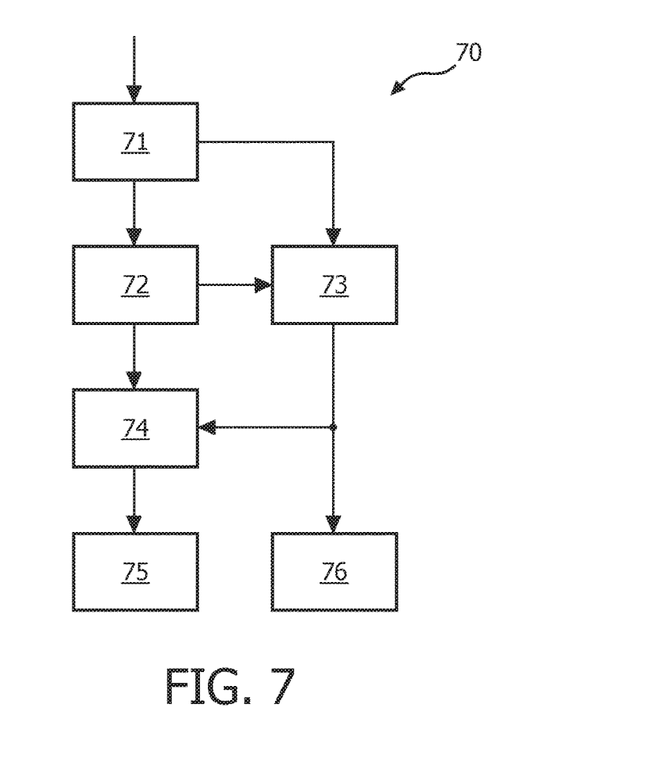
FIG. 7 shows a flow chart of the method for determining the occurrence of a QRS complex in ECG data according to the present embodiment.

Firstly, the receiving unit 61 receives a first to twelfth sets of ECG data that are acquired by respectively standard twelve electrode leads (step 71 in the flow chart of FIG. 7).

Next, similar to step 52 in FIG. 5, the detecting unit 62 evaluates the first to twelfth sets of ECG data so as to detect whether or not a QRS complex occurs within a predefined temporal window in the respective sets of ECG data (step 72 in the flow chart of FIG. 7).

Subsequently, the calculation unit 63 derives a first to twelfth signal quality values V respectively for each of the first to twelfth sets of ECG data (step 73 in the flow chart of FIG. 7). Since the step of deriving the signal quality values is similar to that described in conjunction with step 54 of FIG. 5, a detailed description thereof is omitted herein for conciseness.

After the first to twelfth signal quality values have been derived, the comparison unit 64 compares the first to twelfth signal quality values V with each other and determines three sets of ECG data whose signal quality values V are the smallest among the first to twelfth sets of ECG data (step 74 in the flow chart of FIG. 7).

In other words, according to the ratio values, the three leads having the smallest ratios are selected as the promising leads for QRS detection. Similarly, if a QRS complex has been detected within the predefined temporal window in at least two of the determined three sets of ECG data, the output 65 will output a message indicating an occurrence of a QRS complex within the predefined temporal window (step 75 in the flow chart of FIG. 7), so that the apparatus 224 confirms the reliability of the detected beats and may then further determine the beat location accordingly.

In other words, the apparatus 224 shown in FIG. 6 is different from that shown in FIG. 4 in that the electrode leads to be used for QRS detection are not fixedly selected but are selected according to the signal quality values of the ECG data acquired by the leads. From a theoretical point of view, the performance of this type of apparatus 224 is better than that of the first type due to the adaptive feature. However, from a complexity point of view in practical application, the first type of identifier is more suitable since it is much simpler in terms of its algorithm.

Similarly, as an optional component, the apparatus 224 shown in FIG. 6 may further comprise an interface unit 66, which is configured to output a warning message when one of the first to twelfth signal quality values V is greater than a predetermined threshold (step 76 in the flow chart of FIG. 7).

In this way, the clinical staff may be notified in time that unsatisfactory ECG data has been collected and they may then timely check whether this is due to the loss of contact between the leads and the subject or due to other reasons.

Figure 8:
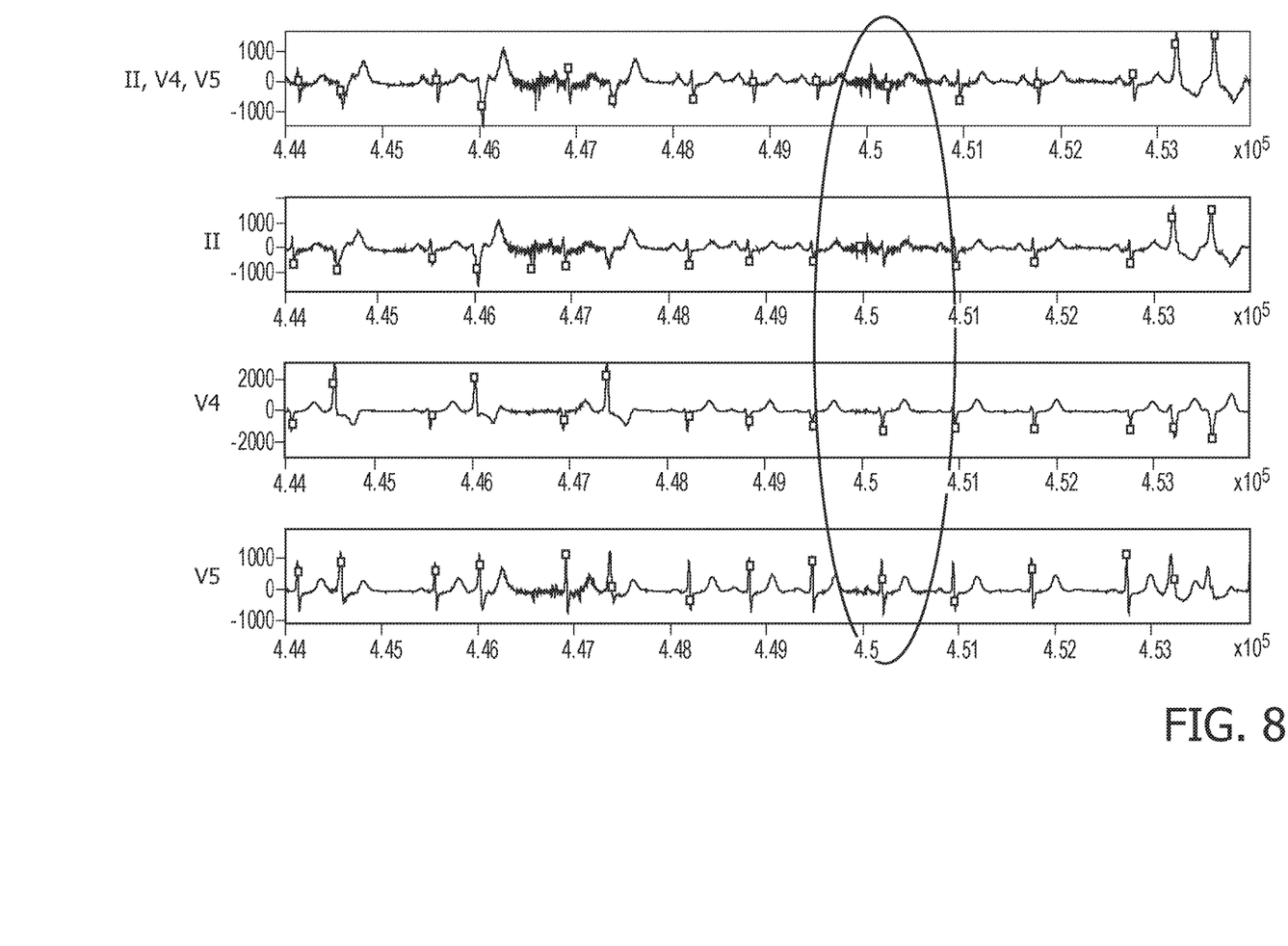
FIGS. 8-9 show the performance improvement when the apparatus of the present invention is utilized in the ECG monitoring system.
Figure 9:
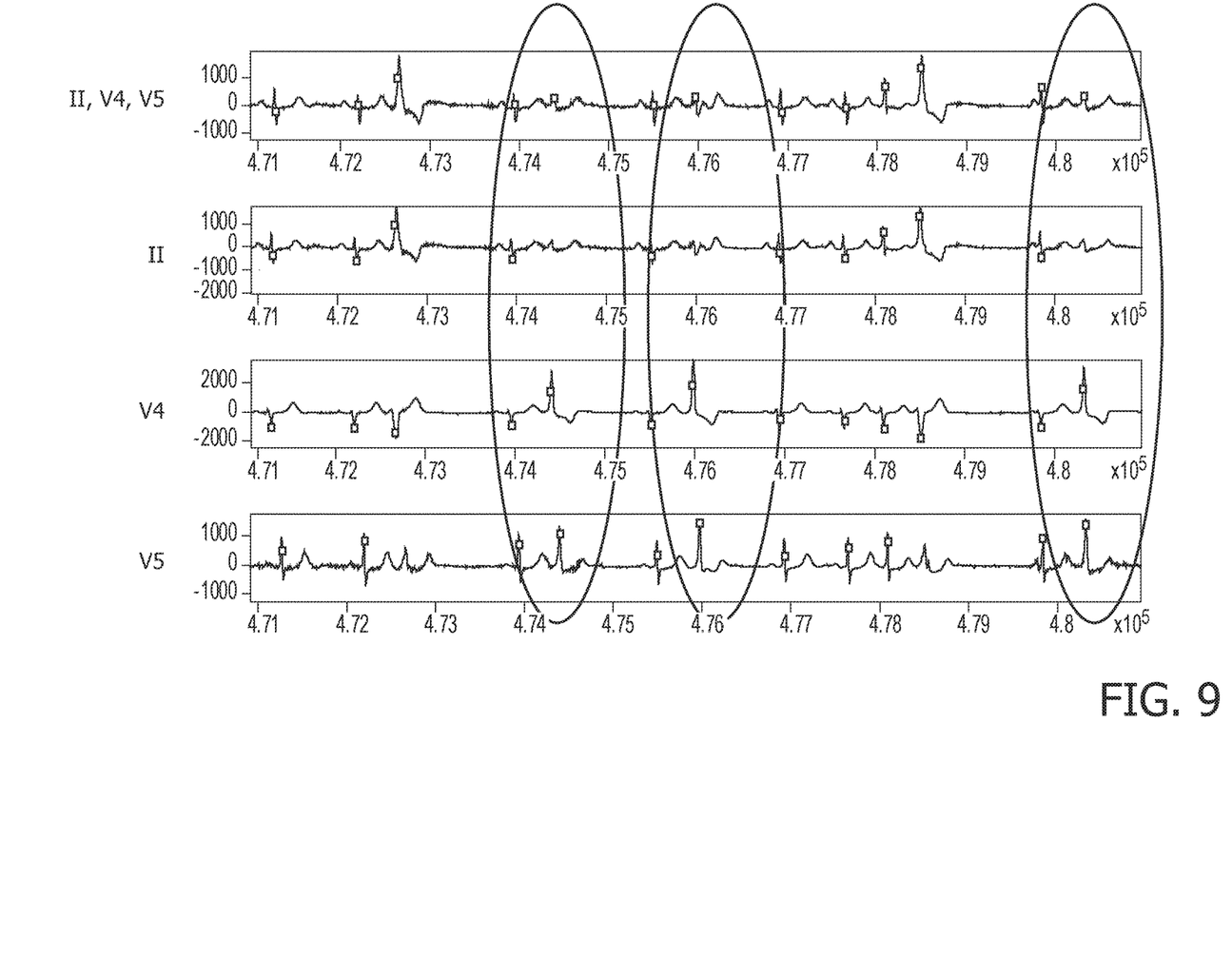

FIGS. 8 and 9 show the performance improvement of the present invention, for example when leads II, V4 and V5 are selected as the leads for QRS complex detection, which is verified by clinical testing on volunteer cases and patient cases at Hoag Hospital, Newport Beach, Calif.

In FIGS. 8 and 9 are shown, from top to bottom, improved beat detection based on the selected leads II, V4 and V5; R detection in lead II only; R detection in lead V4 only; and R detection in lead V5 only.

From FIGS. 8 and 9, it can be clearly seen that by using the invented apparatus, the falsely detected beat in lead II can be avoided (FIG. 8), and at the same time the missed true beat can be detected (FIGS. 8 and 9). Compared with the traditional way of using leads II, aVF and V5 as the fixed leads for QRS beat detection, the missed PVC-like beat can be detected when use is made of the invented signal quality dependent identifier (refer to FIG. 1 and FIG. 9).

Table 1 further illustrates the evaluation of the invented apparatus by using the clinical data collected at Hoag Hospital. The ECG signal was sampled at 1000 samples per second and an amplitude resolution of 5 µV per least significant bit. The subjects were between 24 and 82 years of age. The tests covered 4 exercise stages and recovery stages, the duration varied between 312 and 1091 minutes according to the subjects' conditions. By visually analyzing a total of 28,960 beats, the achieved detection error is 0.19 percent, and the sensitivity of the invented beat identifier is 99.81 percent.

TABLE 1

Verification subjects: 23 patient data from Hoag.

| Patient ID | Total beats | False & Missed beats | Ratio (False & missed beats/total beats) | Ratio (True beats/total beats) |
| --- | --- | --- | --- | --- |
| HH_01 | 952 | 3 | 0.32% | 99.68% |
| HH_02 | 1381 | 5 | 0.36% | 99.64% |
| HH_03 | 556 | 0 | 0% | 100% |
| HH_04 | 783 | 2 | 0.26% | 99.74% |
| HH_05 | 703 | 0 | 0% | 100% |
| HH_06 | 1164 | 0 | 0% | 100% |
| HH_07 | 1635 | 2 | 0.12% | 99.88% |
| HH_08 | 1244 | 13 | 1.05% | 98.95% |
| HH_09 | 1447 | 0 | 0% | 100% |
| HH_10 | 881 | 1 | 0.11% | 99.89% |
| HH_11 | 1612 | 0 | 0% | 100% |
| HH_12 | 1184 | 1 | 0.08% | 99.92% |
| HH_13 | 1696 | 0 | 0% | 100% |
| HH_14 | 709 | 0 | 0% | 100% |
| HH_15 | 1577 | 0 | 0% | 100% |
| HH_P01 | 554 | 12 | 2.17% | 97.83% |
| HH_P02 | 1655 | 5 | 0.3% | 99.7% |
| HH_P03 | 1465 | 3 | 0.2% | 99.8% |
| HH_P04 | 2273 | 0 | 0% | 100% |

TABLE 1-continued

Verification subjects: 23 patient data from Hoag.

| Patient ID | Total beats | False & Missed beats | Ratio (False & missed beats/total beats) | Ratio (True beats/total beats) |
| --- | --- | --- | --- | --- |
| HH_P05 | 905 | 4 | 0.44% | 99.56% |
| HH_P06 | 1795 | 5 | 0.28% | 99.72% |
| HH_P07 | 1502 | 0 | 0% | 100% |
| HH_P08 | 1287 | 0 | 0% | 100% |
| Total | 28960 | 56 | | |
| Ave | | | 0.19% | 99.81% |

As is well-known in the art, although the present invention is directed to improve the detection accuracy for the dominant electrical activity, i.e., QRS complex, in electrocardiograms ("ECG"), especially in the stress test system, including treadmill exercise and ergometer exercise systems, this invention can also be used in medical systems performing ECG analysis, Holter tape analysis, and real-time patient monitoring.

Please note that the steps of the methods shown in the present invention are not to be considered in a limiting sense, as other steps are also possible. It will be apparent to those skilled in the art that the various aspects of the invention claimed may be practiced in other examples that depart from these specific details.

Furthermore, as can be easily understood by the person skilled in the art, in the apparatus claim enumerating several means, several of these means can be embodied by one and the same item of hardware. The mere fact that certain measures are recited in mutually different dependent claims does not indicate that a combination of these measures cannot be used to advantage.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The usage of the words first, second and third, et cetera, does not indicate any ordering. These words are to be interpreted as names.

The invention claimed is:

1. An apparatus for detecting the occurrence of a QRS complex in ECG data acquired from a subject being monitored, comprising:
    a receiving unit configured to receive a first to twelfth sets of ECG data that are acquired by respectively standard twelve electrode leads attached to the subject;
    a detecting unit configured to evaluate the first to twelfth sets of ECG data so as to detect whether or not a QRS complex occurs within a predefined temporal window in the respective set of ECG data;
    a calculation unit configured to derive a first to twelfth signal quality values V respectively for each of the first to twelfth sets of ECG data by calculating the ratio of standard deviation of N consecutive waveforms in the respective set of ECG data to a reference standard deviation of the respective set of ECG data or by calculating the ratio of signal energy ratio (SNR) of N consecutive waveforms in the respective set of ECG data to a reference SNR of the respective set of ECG data, wherein the reference standard deviation and the reference SNR of the respective set of ECG data are predetermined from respectively a first to twelfth sets of ECG data that are acquired by respectively standard twelve electrode leads at the pre-exercise stage;

a comparison unit configured to compare the first to twelfth signal quality values V and determine three sets of ECG data whose signal quality values V are the smallest among the first to twelfth sets of ECG data; and an output configured to output a message indicating an occurrence of a QRS complex within the predefined temporal window if a QRS complex has been detected within the predefined temporal window in at least two of the determined three sets of ECG data.

2. The apparatus according to claim 1, further comprising:
an interface unit configured to output a warning message when one of the first to twelfth signal quality values V is greater than a predetermined threshold.

3. A method for detecting the occurrence of a QRS complex in ECG data acquired from a subject being monitored, comprising:

receiving a first to twelfth sets of ECG data that are acquired by respectively standard twelve electrode leads attached to the subject;

evaluating the first to twelfth sets of ECG data so as to detect whether or not a QRS complex occurs within a predefined temporal window in the respective set of ECG data;

deriving a first to twelfth signal quality values V respectively for each of the first to twelfth sets of ECG data by calculating the ratio of standard deviation of N consecutive waveforms in the respective set of ECG data to a reference standard deviation of the respective set of ECG data or by calculating the ratio of signal energy ratio (SNR) of N consecutive waveforms in the respective set of ECG data to a reference SNR of the respective set of ECG data, wherein the reference standard deviation and the reference SNR of the respective set of ECG data are predetermined respectively from a first to twelfth sets of ECG data that are acquired by respectively standard twelve electrode leads at the pre-exercise stage;

comparing the first to twelfth signal quality values V and determining three sets of ECG data whose signal quality values V are the smallest among the first to twelfth sets of ECG data; and outputting a message indicating an occurrence of a QRS complex within the predefined temporal window if a QRS complex has been detected within the predefined temporal window in at least two of the determined three sets of ECG data.

4. The method according to claim 3, further comprising:
outputting a warning message when one of the first to twelfth signal quality values V is greater than a predetermined threshold.

* * * * *